United States Patent [19]
Howard, III et al.

[11] Patent Number: 6,096,048
[45] Date of Patent: Aug. 1, 2000

[54] NONINVASIVE, REATTACHABLE SKULL FIDUCIAL MARKER SYSTEM

[76] Inventors: Matthew A. Howard, III, 200 Hawkins Dr., Iowa City, Iowa 52242; William E. LaVelle, 11 Glenview Knoll, NE.; Matthew B. Dobbs, 2279 Taylor Dr., both of Iowa City, Iowa 52240; Tereasa M. Simonson, 230 N. Stewart St., North Liberty, Iowa 52317

[21] Appl. No.: 08/230,526

[22] Filed: Apr. 20, 1994

[51] Int. Cl.⁷ ................................. A61B 19/00
[52] U.S. Cl. ................... 606/130; 600/426; 600/429; 600/414; 600/417
[58] Field of Search .............. 606/1, 130; 604/116; 433/213, 214; 600/417, 429, 426, 414

[56] References Cited

U.S. PATENT DOCUMENTS

| | | | |
|---|---|---|---|
| 3,200,497 | 8/1965 | Goodfriend | 433/214 |
| 3,614,950 | 10/1971 | Rabey | 606/130 |
| 4,602,622 | 7/1986 | Bar et al. . | |
| 4,841,965 | 6/1989 | Jacobs . | |
| 5,207,688 | 5/1993 | Carol . | |
| 5,230,623 | 7/1993 | Guthrie et al. | 433/72 |
| 5,330,485 | 7/1994 | Clayman et al. | 606/1 |
| 5,380,336 | 1/1995 | Misko et al. | 606/130 |
| 5,387,220 | 2/1995 | Pisharodi | 606/130 |

FOREIGN PATENT DOCUMENTS

| | | | |
|---|---|---|---|
| 3540756 | 5/1987 | Germany | 433/214 |
| 4211017 | 10/1993 | Germany | 433/214 |
| 4211018 | 10/1993 | Germany | 433/214 |
| 1666093 | 7/1991 | U.S.S.R. | 606/130 |
| 2213066 | 8/1989 | United Kingdom | 606/130 |

OTHER PUBLICATIONS

Maurer, Jr. et al., A Review of Medical Image Registration, in Interactive Image–Guided Neurosurgery (AAN Publications Committee, Robert J. Maciunas, MD, ed.) 17–44 (1993).

*Primary Examiner*—Glenn K. Dawson
*Attorney, Agent, or Firm*—James Creighton Wray; Meera P. Narasimhan

[57] ABSTRACT

A frameless stereotaxis skull fiducial marker system uses custom-formed mouthpieces fitted to maxillary and mandibular teeth. A relatively thick medial portion of a tapered U-shaped bar is attached to a forward projecting connector on a mouthpiece. Thin distal ends of the rigid U-shaped bar support fiducial markers. The customized mouthpiece is stored for repeated use on a patient. The rigid bar may be connected to mouthpieces customized for several patients.

11 Claims, 2 Drawing Sheets

NONINVASIVE, REATTACHABLE SKULL FIDUCIAL MARKER SYSTEM

BACKGROUND OF THE INVENTION

This invention relates to fiducial markers for frameless stereotaxis and magnetic surgery.

Stereotaxic neurosurgery is evolving rapidly due in large part to the development of fast, powerful computers and innovative imaging and interactive image-guided neurosurgical techniques. The ability of the modern computer to quickly execute complex geometric calculations is being harnessed to provide spatial information which in the past could only be obtained by using precisely machined mechanical devices attached to rigid frames.

One of the most active areas of development in stereotaxic neurosurgery today is frameless stereotaxis (FS) and related imaging technologies. The fundamental concept behind the various FS systems is to provide the surgeon with precise intracranial localization information without the use of a conventional fixed head frame.

Frameless stereotaxic treatment methods require that the position of the skull be accurately registered during surgery. A widely used and efficient approach to achieving this objective was to use a number of clearly defined points on the skull as registration markers. These points must be clearly visible on the pre-operative MRI or CT scan and during the treatment phase of the procedure. The ideal registration method would be safe, noninvasive and highly accurate.

The process of intraoperative localization is carried out as follows. First, the patient undergoes a computer tomography (CT) or magnetic resonance imaging (MRI) with fiducial markers in place. These fiducial markers must be in fixed positions relative to the skull and are made of materials that are clearly visible on the preoperative imaging studies. During surgery, the patient's head is secured in place so that it does not move relative to a frameless position sensing system. A variety of sensing systems are currently in use, mechanical translation devices, ultrasonic sound detectors, and infrared light detectors, for example, to precisely determine the location of a hand-held locating wand within a three-dimensional volume. The locations of the patient's brain structures within the three-dimensional volume are determined by first delineating the fiducial marker locations with the localizing wand, and then touching the particular intracranial point in question. After the fiducial point locations have been logged in, the FS computer determines where the wand tip is relative to the preoperative imaging study and displays this information to the surgeon.

To make clinical use of preoperative MRI or CT data, the frameless stereotaxis computer must be given accurate information concerning the patient's head position during both the preoperative radiologic study and the surgical or radiation treatment. Traditional rigid frames attached to the skull subserve this function adequately (e.g. BRW or Lexel headframes). With the evolution of frameless stereotaxis methods, however, these well proven spatial reference systems have excess structural capacity that is unnecessary and cumbersome.

Fiducial skull markers play a critical role in this process. They must be well visualized and remain stationary relative to the skull from the time the imaging study is obtained to the time surgery is conducted. One approach used is to screw the markers into the skull. This can be carried out under local anesthesia as a minor operation. This approach has the advantage of great precision and the disadvantages of being an invasive procedure and having a time limitation in their use. Infection risk increases with chronic insertion. The other widely used method is to glue markers to the scalp. This approach has the advantage of being noninvasive, and the disadvantage of a relatively unstable mechanical purchase on the skin. The markers might become dislodged during the time interval between the imaging study and surgery.

Numerous "frameless" registration methods have been developed to encode head position information more efficiently. A fundamental requirement for all these methods is that at least three discrete points positioned on or around the patient's head must be visible on the preoperative imaging studies and during the treatment phase. Noninvasive methods, such as identifying skull surface features or gluing fiducial markers to the scalp, represent a significant improvement in patient comfort but are not as consistently accurate as methods using rigid points of skull fixation. The greatest degree of accuracy has been achieved using markers that are screwed into the skull. Although these markers can be inserted quickly with minimal inconvenience to the patient, they are invasive and cannot be left in place for extended periods of time.

As defined in a recent review of medical image registration techniques, "extrinsic" point methods means man-made fiducial objects are attached to the skull. A wide range of noninvasive extrinsic marker methods have been used, including skin staples and spheres glued to the scalp. Methods based on skin fixation have the advantages of safety and ease of use. Skin is not rigidly attached to the skull, however, and is thus susceptible to slight shifts in position. Also, spheres glued to the scalp may occasionally be dislodged and are not designed for long-term fixation. Markers screwed into the skull are highly accurate and mechanically stable. Because of their invasive nature, however, there is a small surgical risk associated with their use. Patients experience mild discomfort during the insertion procedure, and there is no opportunity for convenient reapplication during serial studies spanning several weeks to months.

A need exists for a new skull fiducial marker system which can be used for frameless stereotaxic and magnetic neurosurgery, serial and cross-modality volumetric diagnostic imaging, as well as focused radiation therapy. A need exists for systems which fix rigidly to the skull, are simple to use, are noninvasive, are reattachable over long periods of time, and have submillimetric accuracy.

SUMMARY OF THE INVENTION

This invention fulfills the needs and provides noninvasive reattachable fiducial markers for frameless stereotaxis and magnetic surgery.

The present invention is a simple, inexpensive device designed to precisely position cranial fiducial markers about a patient's head for purposes of frameless stereotaxis or magnetic neurosurgery. The distinct advantages of the invention relative to existing fiducial marker systems include ease of application, a completely noninvasive approach, and the ability to precisely reposition over long periods of time.

One of the most important requirements for the current system was to identify a region of the skull rigidly fixed in place relative to the brain, and onto which a lightweight fiducial marker device could be reversibly attached. The skull attachment had to be secure, yet had to be capable of being removed and later reattached with the device assuming the exact same spatial orientation relative to the skull with each use. A device fulfilling these criteria has been created to attach to the hard palate and maxillary teeth. Counterpressure is provided by the mandibular teeth. Because of the device's shape and site of attachment, the invention is fixed rigidly to the skull, is simple to use, is noninvasive, is reattachable over long periods of time, and has submillimetric accuracy.

A practical noninvasive, reattachable fiducial system of achieving rigid, reversible skull fixation without penetrating the skin or causing discomfort to the patient uses the maxillary teeth. They are rigidly fixed to the skull and can withstand significant mechanical pressure over extended periods of time without injury. The rich topography of the occlusal portions of the teeth allows individualized precision molds to be formed that are rigidly fixed when placed in the mouth. The primary surface of fixation is the maxillary teeth. The mandibular teeth exert a small amount of pressure on the custom contoured underside of the mouthpiece to insure absolute stability without discomfort. In the fields of dentistry and maxillofacial reconstructive surgery, the accuracy with which custom maxillary and mandibular teeth molds can be reattached has been clearly demonstrated.

Teeth within the maxilla are absolutely stationary relative to the cranial vault. A molded mouthpiece can be created which precisely and reversibly fits onto the teeth with submillimeter precision.

A frameless stereotaxis skull fiducial marker system uses custom-formed mouthpieces fitted to maxillary teeth with counter pressure being applied by the mandibular teeth pressing on a countoured mold. A relatively thick medial portion of a tapered U-shaped bar is attached to a forward projecting connector on a mouthpiece. Thin distal ends of the rigid U-shaped bar support fiducial markers. The customized mouthpiece is stored for repeated use on a patient. The rigid bar may be connected to mouthpieces customized for several patients.

The invention has two parts: a customized detachable mouthpiece, and a reusable curved lightweight metal banana-shaped bar that locks onto the mouthpiece and functions as an anchor for screw-in fiducial markers. There are no forces other than gravity exerted on the banana-shaped bar during use. The assembly is not used to hold the patient's head stationary. The assembly remains absolutely rigid during all phases of its use.

A U-shaped fiducial bar is attached to the new mouthpiece and serves as a purchase site for interchangeable screw-in fiducial markers. The simple design and light weight of the fiducial bar is feasible because it serves no cranial fixation or stabilization function, thus gravity is the only force the bar must withstand. Attaching the invention onto the skull is as simple as inserting an athletic mouthpiece. Torque exerted on the mouthpiece is less than that produced by a typical smoking pipe.

A custom mouthpiece is constructed for the patient by placing the appropriate dental cement onto the top and bottom of the mouthpiece. A patient bites down on the mouthpiece. After the cement hardens, a rigid, removable mouthpiece is ready for use. That aspect of the invention has been perfected through many years of clinical use in maxillo-facial reconstructive surgery. The mouthpiece is secured to the curved bar, and the entire device is then placed back into the patient's mouth. The fiducial markers are screwed into the distal aspects of the bar and are held rigidly in place relative to the skull.

A CT scan or MRI is obtained with the mouthpiece and banana-shaped bar in position. After the scan, the mouthpiece is removed from the patient's mouth. The mouthpiece is removed from the curved bar. Both are safely stored with careful attention being paid to avoid exerting any forces on the apparatus that might cause warping.

At the time of surgery, the bar is assembled on the mouthpiece which is placed back into the patient's mouth. The fiducial markers are used in the same fashion as conventional markers. The bar may be used with mouthpieces for different patients. Because the bar is relatively inexpensive, it may be left attached to the mouthpiece and stored with the mouthpiece for future use. Markers either may be left on the bar or may be removed from the bar for separate storage or use.

A fiducial bar is reusable. A detachable mouthpiece is custom built for each patient. The mouthpiece is a C-shaped plate with a precisely machined extension for attachment to the fiducial bar. A customized fit is achieved by placing quick curing dental cement on the maxillary and mandibular sides of the mouthpiece and then having the patient bite down. An exact cast of the maxillary and mandibular teeth is produced, which allows rigid, reproducible fixation of the mouthpiece. The extra-oral portion of the mouthpiece is machined to fit precisely into the fiducial bar using a guide pin and two securing screws. When the bar is fixed in position, the fiducial bar curves back along the side of the patient's head. The bar is thickest closest to the mouthpiece to resist torque, and then is gradually tapered back in a smooth curve. Threaded openings are positioned along the bar to serve as reversible insertion sites for screw-in plastic fiducial markers. Depending on the application, the screw-in markers contain metal, high contrast liquid, or mechanical point indicators.

The ideal construction material for the invention is a strong, rigid, lightweight plastic that generates no signal on an MRI study. The rigidity and strength requirements are modest and can be met by many materials, because the only force acting on the structure is gravity. The simple monoplanar fiducial bar design also allows easy storage in a position that will not encourage shrinking, creeping, twisting or warping over time.

A prototype was constructed using lightweight aluminum and plexiglass. A simple but highly accurate optical imaging method was devised to determine the positioning accuracy of the invention during serial cranial reattachments.

A simple optical sighting method tested the repositioning accuracy of the invention during serial reapplications on different subjects. By visually aligning two dots placed at either end of a transparent siting marker, serial photographs were taken at the same angle relative to the new marker system. Using this method in conjunction with a scaling transformation, comparative measurements were made between the fiducial markers and unique points on the subject's ear. The ear is in a fixed position relative to the skull, and direct visualization methods avoid inaccuracies inherent in computer-generated imaging techniques (e.g. CT scan, MRI). Although the new method was devised to provide an objective measure of the repositioning accuracy of the new marker system, the same simple technique could also be used clinically in the future to confirm repositioning accuracy in individual patients prior to initiation of treatment.

Optical imaging was used because measurements derived from direct visualization of a structure are more spatially accurate than those derived from a computer-generated CT or MRI scan. In the clinical applications envisioned for the invention, the target of interest is the brain, a structure which cannot be directly visualized under normal circumstances. For purposes of testing the repositioning accuracy of fiducial markers, however, it is feasible to make optical measurements relative to a different anatomical structure which is directly visible and equally well secured to the skull. In the current study, the ear served that function. The ear, when observed from the lateral view, has rich topographic features that allow for selection of unique points that can be reidentified on serial views with submillimetric accuracy.

The measuring technique used required that photographs be taken at the same angle relative to the new marker system during serial reapplications. Proper angular alignment was achieved using a "gun-site" method. On each side of the patient's head, a modified 2.5 cm fiducial marker was inserted as an angular alignment device. One millimeter diameter black dots were positioned along the central axis at either end. By orienting the camera such that the two dots overlapped, a reproducible angle was defined. Uniformity of photographic magnification was insured by referencing all measurements to a millimeter scale etched onto the side of the new marker system bar.

Repositioning accuracy was tested with five volunteers using five custom mouthpieces and one prototype bar. As described above, left and right lateral view photographs were taken of each volunteer with the new marker system in place at weekly intervals over a three week period in four sessions. Shifts in position between the fiducial markers and the ear were analyzed by measuring distances between unique ear points and the fiducial markers. Repositioning accuracy was statistically analyzed using the analysis of variance method.

The prototype of the invention was easy to use. The prototype was machined of lightweight aluminum. A detachable mouthpiece was secured to the fiducial bar with a guide post and securing screws. The mouthpiece was easily removed and reattached in less than two minutes using a screwdriver. No measurable warping or bending of the apparatus occurred during the three week trial period, despite multiple attachments and reattachments of five different mouthpieces. The invention was convenient to use. Customized mouthpieces were produced in a few minutes without need of any specialized support equipment. The new marker system mouthpieces attached securely and comfortably to the maxillary teeth. The fiducial bar weighs 60 grams, 3 grams less than a standard briar pipe, and was held in place comfortably for time periods exceeding 30 minutes.

The invention provides repositioning accuracy. A simple fiducial system is secured to the maxillary teeth as described, and the results of prototype testing were successful. The new system is inexpensive to produce, is simple to use, is noninvasive, is reattachable and results in highly accurate placement of fiducial points about the skull.

Over a three week period during which time the new marker system was subject to 20 mouthpiece insertions and removals, there was no detectable warping or bending of the prototype. Fiducial marker repositioning accuracy was submillimetric, which compares favorably with existing invasive, non-reattachable techniques.

The invention was originally made for use during magnetic surgery; an application where a small remotely controlled vehicle is moved magnetically to selected brain target sites for diagnostic and therapeutic purposes. The ability to move an implant serially without re-operation is a unique feature of magnetic surgery. To optimize this capability, a noninvasive fiducial system was needed that could be precisely reapplied during serial magnetic manipulations.

While initially intended for magnetic surgery, several design features of the new marker system suggest its potential applicability in a variety of clinical applications where precision noninvasive serial imaging is needed, including interactive image-guided neurosurgery, serial volumetric analysis of normal and pathological brain structures, focused and multiple treatment radiation therapy, and cross-modality volumetric correlations, e.g. MRI, CT, PET.

The current results using an aluminum prototype are encouraging. Several caveats must be considered. First, the new system should only be used in patients with stable maxillary teeth. Second, the current report demonstrates the accuracy of the new system in consistently repositioning fiducial markers in exact locations about the skull. While it seems likely this repositioning accuracy can be effectively incorporated into an accurate treatment system, the issue will not be clarified until actual clinical trials are completed.

While the prototype is aluminum, a reinforced plastic marker system is preferred.

The invention provides a frameless stereotaxis skull fiducial marker system uses custom-formed mouthpieces fitted to maxillary teeth. A relatively thick medial portion of a tapered U-shaped bar is attached to a forward projecting connector on the mouthpiece. Thin distal ends of the rigid U-shaped bar support fiducial markers. The customized mouthpiece is stored for repeated use on a patient. The rigid frame may be connected to mouthpieces customized for several patients.

The preferred skull fiducial marker apparatus has a custom mouthpiece for attachment to the maxilla of a patient. A projection extends forward from the mouthpiece. A curved U-shaped bar has a medial portion connected to a front of the forward projection. The bar and the front projection are removably attached. The forward projection extends into a recess in the bar. The bar is relatively thick at its medial portion and tapers to relatively thin distal ends. The U-shaped bar has remotely positioned distal portions for receiving fiducial markers. Fiducial markers are connected to the distal portions of the bar.

The preferred fiducial marker attachments are threaded openings in distal ends of the bar, and the fiducial markers have threaded studs for securing in the threaded openings.

In a preferred form of the invention, a skull fiducial marker apparatus is used with a curved bar. A curved bar fiducial marker support has a proximal mounting portion for connecting to the connector on the mouthpiece, and a distal portion for receiving fiducial markers. The preferred bar is U-shaped, the proximal portion is a middle portion of the U-shaped bar, and the U-shaped distal bar has two remote distal portions with marker attachments on the remote distal portions. The bar is relatively thick at the proximal portion and relatively thin at the distal portion.

A connector on the proximal portion connects to a removable maxillary teeth-connected mouthpiece. The mouthpiece is custom fitted to maxillary and mandibular teeth, and a connector is connected to the mouthpiece for mounting a curved bar.

A preferred skull fiducial marker method includes spreading a settable cement on both sides of a mouthpiece, custom-fitting the mouthpiece to maxillary and mandibular teeth, attaching a proximal portion of a marker bar to a frontal extension on the mouthpiece, and attaching fiducial markers to a distal portions of the marker bar.

After use, the mouthpiece is removed, the bar is detached from the mouthpiece, and the mouthpiece and the bar are separately stored. Before using again, the bar is reattached to the mouthpiece, and the mouthpiece is inserted on the maxillary teeth. The bar is used with other patients by attaching the bar to other custom-formed maxillary teeth fitted mouthpieces. A preferred bar mount attaches a medial portion of a U-shaped bar to the mouthpiece. An optical siteing method is used to confirm repositioning accuracy.

These and further and other objects and features of the invention are apparent in the disclosure, which includes the above and ongoing written specification, with the claims and the drawings.

DETAILED DESCRIPTION OF THE DRAWINGS

Figure 1:
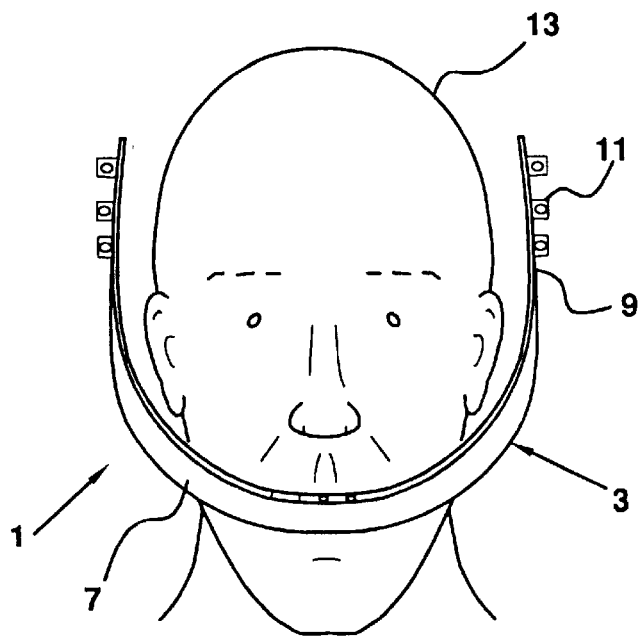
FIG. 1 is a front elevation of the new skull fiducial marker system.
Figure 2:
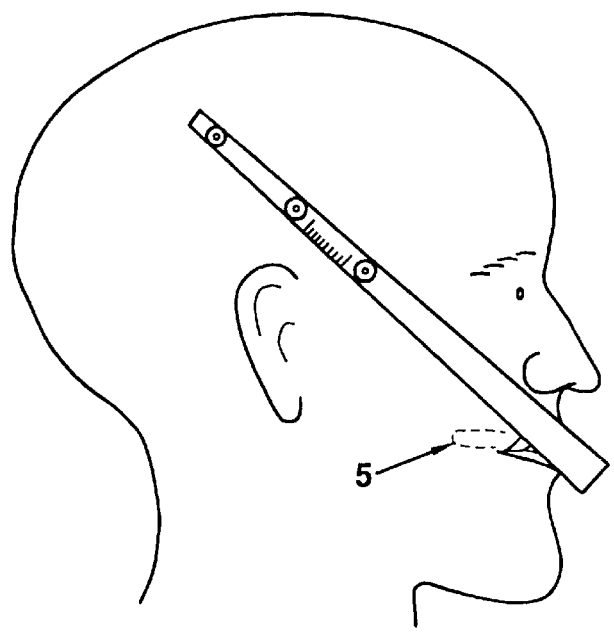
FIG. 2 is a side elevation of the system shown in FIG. 1.

Referring to the drawings, a skull fiducial marker system is generally indicated by the numeral 1. A bar 3 is attached to a forward extension on a mouthpiece 5. The bar 3 is U-shaped or banana-shaped, and has a medial mounting portion 7 which is relatively thick and which tapers outwardly to distal marker portions 9. Markers 11 are placed on the distal portions.

Because the mouthpiece is fixed to the hard maxillary teeth and held in position by the mandibular teeth, the markers 11 are precisely positioned relative to the head 13 of a patient.

Figure 3:
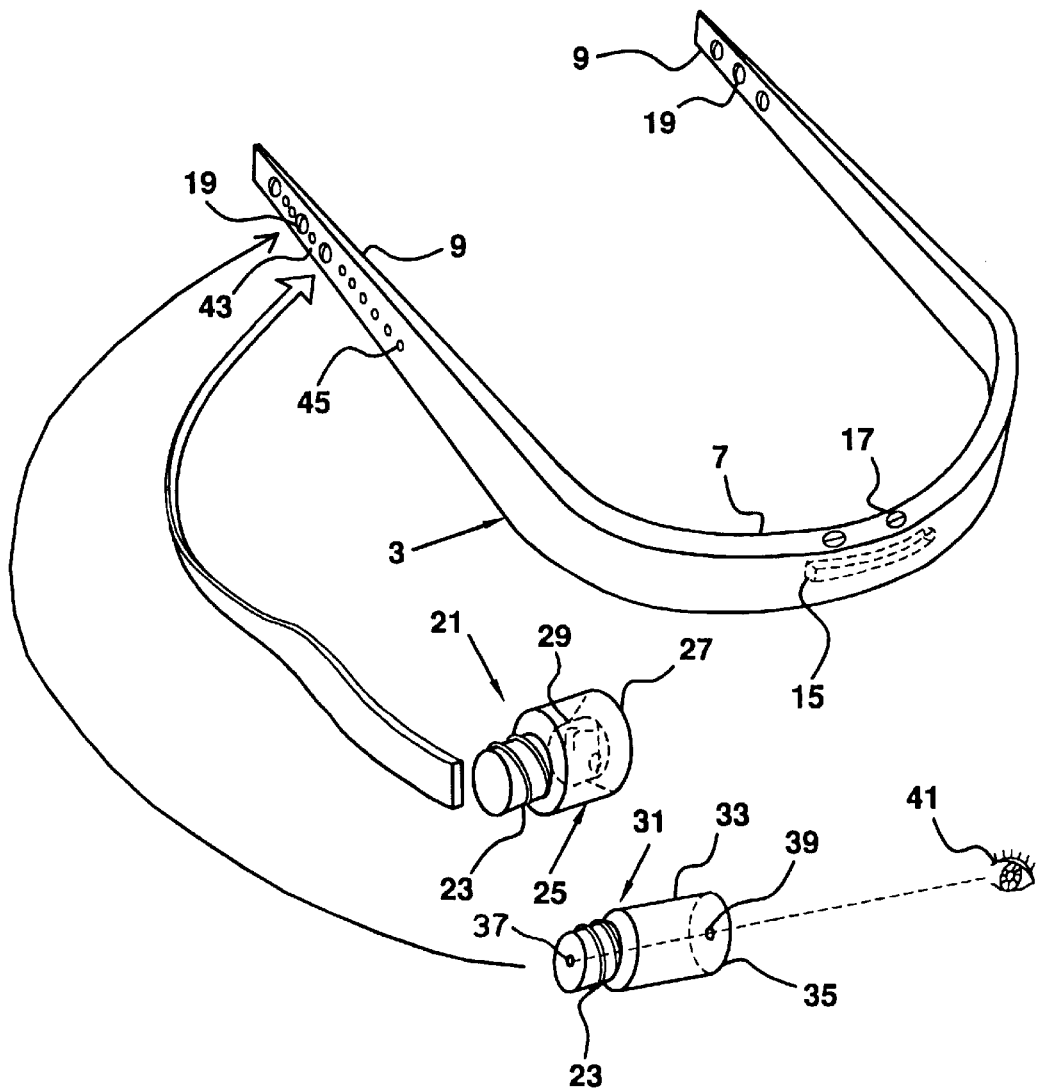
FIG. 3 is a detail of the bar and markers.

FIG. 3 shows a detail of the bar 3. The medial portion 7 has a rearward opening recess 15 in which fits a rigid projection on the mouthpiece. A mouthpiece inserted in the mouthpiece insertion site recess 15 is secured by screws 17. The tapered distal ends 9 have threaded openings 19 for receiving screwed-in fiducial markers 21. The threaded stud ends 23 of the markers screw into the threaded openings 19 in the distal ends 9 of the bar. Marker 25 is a radiographic fiducial marker with a cylindrical body 27, in which a finite source 29 of weak radiation is positioned. The source 29 may continuously emit a weak radiation, or may emit radiation in response to illumination by appropriate energy. An energy opaque marker may be used. Any marker which provides an indication in the scanning record is suitable. The marker 31 is a site alignment fiducial marker, with a hollow barrel 33 filled with a transparent plastic material 35. Marker dots 37 and 39 are positioned on opposite ends of the transparent material for observing alignment with an eye 41.

A scaling bar 43 is printed or engraved in the distal ends 9. Plural holes 45 are formed in the distal ends to reduce weight without reducing strength of the distal ends, and to provide additional reference points or marker attachment points if necessary or useful to reposition the marker.

Figure 4:
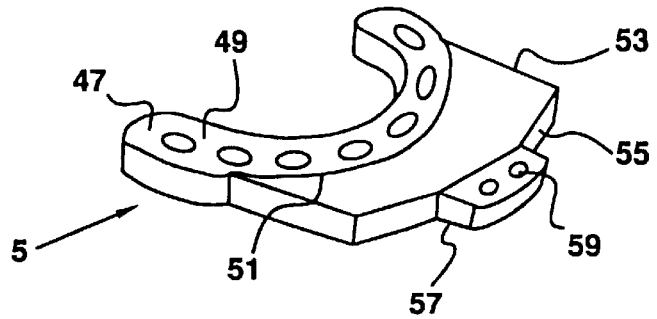
FIG. 4 is a detail of the mouthpiece used in the system shown in FIGS. 1 and 2.

FIG. 4 shows the mouthpiece 5. Mouthpiece 5 holds a hardenable material 47, which has been customized by hardening the material around maxillary and mandibular teeth of a patient, forming the customized tooth-receiving depressions which are schematically shown by the holes 49. The mouthpiece 5 has a front 51 and a projection 53, which projects forward from the front between lips of a patient for attachment to bar 3.

The front face 55 of the projection 53 may be configured for resting against an inner surface of the bar 3. A central projection 57 fits into the recess 15 provided in the medial portion of the bar. Screws 17 connect with openings 59 to rigidly attach the mouthpiece and bar.

While the invention has been described with reference to specific embodiments, modifications and variations of the invention may be constructed without departing from the scope of the invention, which is defined in the following claims.

We claim:

1. A skull fiducial marker apparatus, comprising a custom mouthpiece for attachment to the maxilla of a patient, a projection extending forward from the mouthpiece, a curved U-shaped bar having a medial portion connected to a front of the forward projection for holding the bar spaced from a patient's body, fiducial markers attachable to the U-shaped bar, the U-shaped bar having remotely positioned distal portions for receiving the fiducial markers, wherein the bar is relatively thick at its medial portion, and wherein the bar tapers to relatively thin distal ends.

2. The apparatus of claim 1, wherein the forward projection extends into a recess in the bar.

3. A skull fiducial marker apparatus, comprising a custom mouthpiece for attachment to the maxilla of a patient, a projection extending forward from the mouthpiece, a curved U-shaped bar having a medial portion connected to a front of the forward projection for holding the bar spaced from a patient's body, fiducial markers attachable to the U-shaped bar, the U-shaped bar having remotely positioned distal portions for receiving the fiducial markers, wherein the distal portions of the bar have fiducial marker attachments comprising threaded openings in distal ends of the bar, and wherein the fiducial markers have threaded studs for securing in the threaded openings.

4. Skull fiducial marker apparatus, comprising a bar having a proximal portion and a connector on the proximal portion for connecting to a removable maxillary teeth-connected mouthpiece, the bar having a distal portion and the distal portion having marker areas, wherein the bar is U-shaped, wherein the proximal portion is a medial portion of the U-shaped bar, and wherein the U-shaped bar has two spaced distal portions with fiducial marker areas, wherein the bar is relatively thick at the proximal portion and relatively thin at the distal portions.

5. The apparatus of claim 4, wherein the marker areas on the distal portion of the bar comprise receivers for receiving fiducial markers.

6. A skull fiducial marker method, comprising custom-fitting a mouthpiece to maxillary and mandibular teeth, attaching a proximal portion of a marker bar to the mouthpiece, and attaching fiducial markers to a distal portion of the marker bar, wherein the bar is U-shaped and wherein attaching of the bar comprises attaching a medial portion of the U-shaped bar to the mouthpiece, and further comprising marking distal ends of the U-shaped bar, wherein the marking comprises screwing fiducial marker modules into threaded recesses in the bar.

7. A skull fiducial marker method, comprising custom-fitting a mouthpiece to maxillary and mandibular teeth, attaching a proximal portion of a marker bar to the mouthpiece, and attaching fiducial markers to a distal portion of the marker bar, wherein the attaching of fiducial markers comprises screwing threaded stud portions of marker bodies into threaded openings in the distal portion.

8. The method of claim 7, further comprising removing the mouthpiece and detaching the bar from the mouthpiece, and separately storing the mouthpiece and the bar, reattaching the bar to the mouthpiece and inserting the mouthpiece on the maxillary teeth.

9. The method of claim 7, further comprising attaching the bar to the maxillary and mandibular teeth fitted mouthpiece, and wherein the mouthpiece is adapted to accommodate an endotracheal tube.

10. The method of claim 7, wherein the curved bar is U-shaped and wherein attaching of the bar comprises attaching a medial portion of the U-shaped bar to the mouthpiece, and further comprising marking distal ends of the U-shaped bar.

11. The method of claim 7, further comprising removing the mouthpiece from the bar and attaching the bar to other custom formed maxillary and mandibular teeth fitted mouthpieces.

* * * * *